(12) United States Patent
Shapiro et al.

(10) Patent No.: US 6,187,029 B1
(45) Date of Patent: Feb. 13, 2001

(54) PHOTO-THERMAL TREATMENT DEVICE

(75) Inventors: Ronald S. Shapiro; Richard C. Dunlap, both of Toledo, OH (US); David B. Sutton, Monroe, MI (US); Anthony A. Boiarski, Columbus, OH (US)

(73) Assignee: Physician's Technology, LLC, Monroe, MI (US)

( * ) Notice: Under 35 U.S.C. 154(b), the term of this patent shall be extended for 0 days.

(21) Appl. No.: 09/260,778

(22) Filed: Mar. 2, 1999

(51) Int. Cl.[7] ........................................................ A61N 5/00
(52) U.S. Cl. ................................ 607/88; 607/89; 607/96; 607/91
(58) Field of Search .............................. 606/2, 9, 13, 14, 606/27; 607/88–92

(56) References Cited

U.S. PATENT DOCUMENTS

| | | |
|---|---|---|
| 3,900,034 | 8/1975 | Katz et al. . |
| 4,112,923 | 9/1978 | Tomecek . |
| 4,232,678 | 11/1980 | Skovajsa . |
| 4,622,972 | 11/1986 | Giebeler, Jr. . |
| 4,653,495 | 3/1987 | Nanaumi . |
| 4,693,556 | 9/1987 | McCaughan, Jr. . |
| 4,917,084 | 4/1990 | Sinofsky . |
| 5,000,752 | 3/1991 | Hoskin et al. . |
| 5,012,816 | 5/1991 | Lederer . |
| 5,024,236 | 6/1991 | Shapiro . |
| 5,054,486 | 10/1991 | Yamada . |
| 5,059,191 | 10/1991 | Beyer et al. . |
| 5,178,617 | 1/1993 | Kuizenga et al. . |
| 5,259,380 | * 11/1993 | Mendes et al. ....................... 607/115 |
| 5,300,097 | 4/1994 | Lerner et al. . |
| 5,358,503 | * 10/1994 | Bertwell et al. ........................ 606/27 |
| 5,505,726 | * 4/1996 | Meserol ................................... 606/9 |
| 5,616,140 | * 4/1997 | Prescott ................................. 606/10 |
| 5,800,479 | * 9/1998 | Thiberg ................................. 607/88 |
| 5,957,960 | * 9/1999 | Chen et al. ............................ 607/92 |

FOREIGN PATENT DOCUMENTS

| | | |
|---|---|---|
| 2591902 | 6/1987 | (FR) . |
| 2208803 | 4/1989 | (GB) . |
| 746869 | 7/1980 | (RU) . |

OTHER PUBLICATIONS

BioBeam 600, Narrow–Band Low–Level Light Treatment System, Amcor Ltd. Export Division, 1989.
BioBeam 660, The New, Tested Treatment for Severe Acne, Amcor Ltd. Export Division, 2 pages.

* cited by examiner

Primary Examiner—Linda C. M. Dvorak
Assistant Examiner—A. Farah
(74) Attorney, Agent, or Firm—Harness, Dickey & Pierce, P.L.C.

(57) ABSTRACT

An improved photo-thermal treatment device is disclosed which is ergonomically shaped to facilitate photo-thermal treatment of a wide variety of surface portions of the human anatomy. The device incorporates a plurality of spaced infrared diodes which are actuated sequentially so as to inhibit body adaptation which may reduce the effectiveness of the treatment. Additionally, a single point diode is provided at one end of the device which is specifically designed for localized point treatment of other body surface areas.

19 Claims, 3 Drawing Sheets

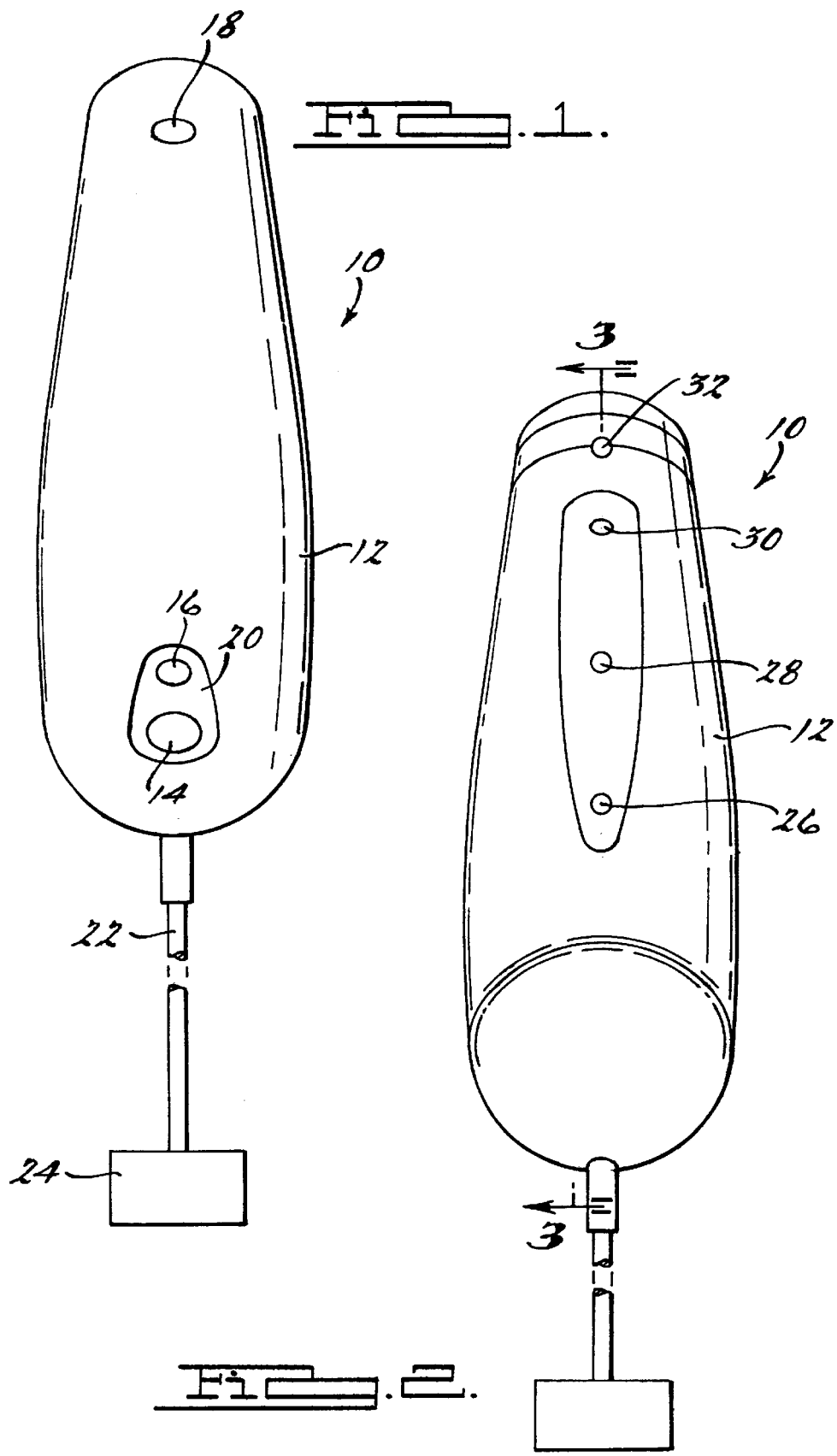

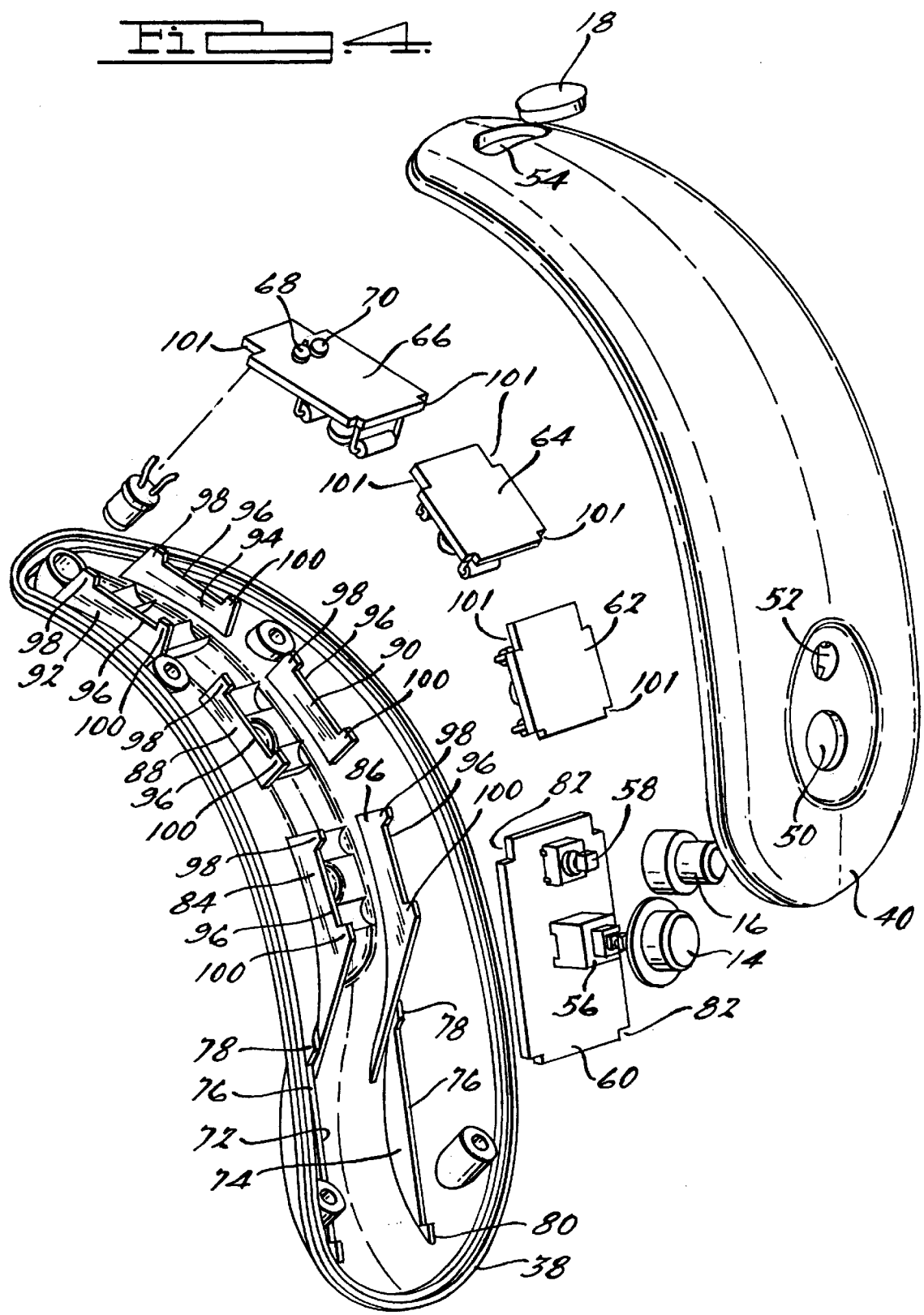

PHOTO-THERMAL TREATMENT DEVICE

BACKGROUND AND SUMMARY OF THE INVENTION

The present invention relates generally to photo-thermal therapeutic devices and more specifically to such a device which incorporates a plurality of light emitting diodes (LEDs) protruding from a specifically contoured housing with the diode spacing and curvature being designed to accommodate treatment of almost any surface of the body for an exceedingly wide range of the population.

The use of light and heat to provide musculoskeletal pain relief, promote cosmetic rejuvenation, promote accelerated healing of open and closed wounds as well as numerous other benefits has long been known. However, devices for use in such treatments have in general been designed for specific applications or been relatively cumbersome to use.

The present invention, however, provides a uniquely designed device for use in photo-thermal treatments which is compact and easy to use while also being contoured to enable it to adapt to most body contours for a wide range of individuals while still providing effective photo-thermal treatment. The contoured housing includes a plurality of LEDs arranged in spaced relationship along a concave surface with a single diode positioned at an outer convex surface area so as to enable the device to treat both large general surface areas as well as specific localized areas. Additionally, the LEDs are preferably designed for sequential firing of spaced pairs of diodes preferably at a frequency in the range of 277 to 307 cycles per second so as to resist body adaptation to the treatment which adaptation may significantly and progressively reduce the effectiveness of the treatment over time.

Additional advantages and features of the present invention will become apparent from the subsequent description and the appended claims taken in conjunction with the accompanying drawings.

BRIEF DESCRIPTION OF THE DRAWINGS

FIG. 1 is an elevation view of the back side of the photo-thermal treatment device shown connected to its remote power supply, all in accordance with the present invention;

FIG. 2 is an elevational view of the device shown in FIG. 1 as seen from the front or treatment side;

FIG. 4 is an exploded perspective view of the device of FIG. 2.

DESCRIPTION OF THE PREFERRED EMBODIMENT

Figure 3:
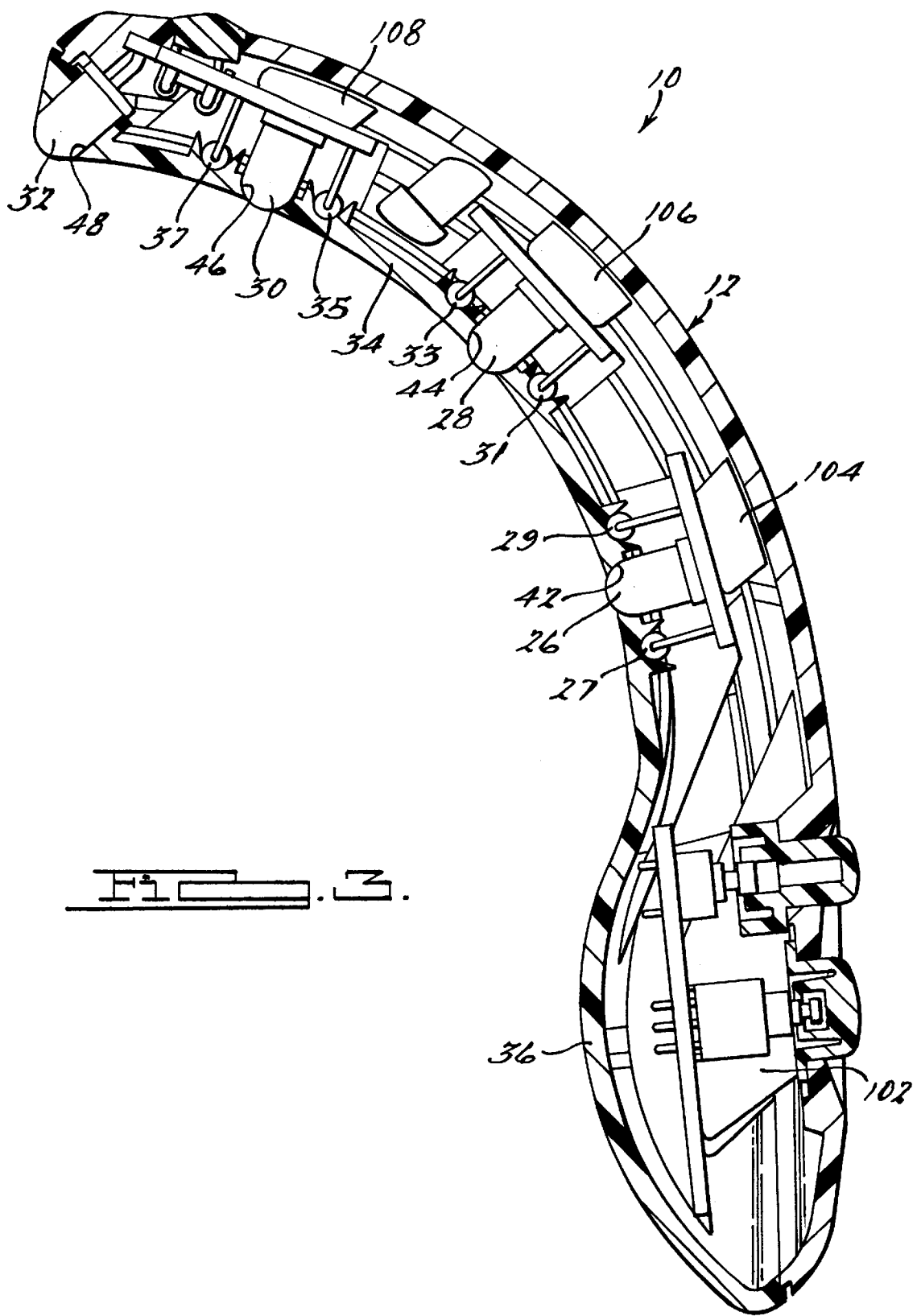
FIG. 3 is a sectional view of the device of FIG. 2, the section being taken along line 3—3 thereof.

Referring now to the drawings and more specifically to FIGS. 1 and 2, there is shown a photo-thermal treatment device 10 in accordance with the present invention. Photo-thermal treatment device 10 includes a contoured housing 12 having an actuation button 14 and a high/low button 16 generally centered on a lower portion of the back surface adjacent one end thereof, and a transparent indicator light lens 18 positioned adjacent the opposite end thereof. Preferably buttons 14 and 16 will be positioned within a slight recess 20 formed on the surface of housing 12 so as to inhibit the inadvertent operation thereof. A power cord 22 extends outwardly from the lower end of housing 12 and is removably connected to a remote power source 24 via a suitable connector. Power source 24 in turn is adapted to be connected to a source of 120 volt 60 hz alternating current and to provide a suitable supply of DC current and voltage to treatment device 12.

As shown in FIG. 2, the front or treatment side of housing 12 includes four light emitting diodes 26, 28, 30, and 32 all of which are positioned in spaced relationship generally along a longitudinal midline of housing 12 with light emitting diode 32 being positioned closely adjacent the upper end of housing 12.

As best seen with reference to FIGS. 1 and 3, housing 12 is preferably formed from a suitable polymeric composition and includes an arcuate upper treatment portion 34 within which light emitting diodes 26, 28, 30 and 32 are positioned and a lower switch portion 36 of slightly increased lateral thickness to accommodate electronic circuitry therein. Preferably treatment portion 34 will have a radius of curvature approximating the average curvature of the top part of the adult human hand in the area of the knuckles, which curvature will also accommodate the average curvature of the wrist, arm and elbow of an adult human as well as other body areas of an adult human. Based upon research to date, it is believed that a radius of curvature of approximately 4.5" gives a treatment portion which is extremely well suited to enable the photo-thermal treatment device of the present invention to be effectively utilized to treat various portions of the human anatomy for individuals over a wide range of stature and build. More specifically, it has been found that this radius of curvature serves to easily and effectively accommodate treatment of the hand, wrist, arm, elbow as well as a variety of other portions of the body.

Housing 12 is designed to be easily formed such as by injection molding or the like and includes inner and outer shell portions 38 and 40 which are designed to be secured together in any suitable manner such as by fasteners or adhesively joined telescoping posts for example. A plurality of openings 42, 44, 46 and 48 are provided positioned in spaced relationship generally along the longitudinal midline of inner shell portion 38 with opening 48 being positioned closely adjacent the upper end thereof. Outer portion 40 also includes a pair of relatively closely spaced openings 50 and 52 opening into recess 20 which openings are adapted to movably receive respective buttons 14 and 16 and a third opening 54 positioned adjacent the opposite end thereof within which transparent lens 18 is fitted.

In order to augment the thermal treatment effects offered by diodes 26, 28, and 30, a plurality of resistors 27, 29, 31, 33, 35 and 37 are provided being positioned in pairs on opposite sides of respective diodes 26, 28, and 30. Preferably these resistors will be positioned with the heat generating resistive coil portion in contact with housing 34 immediately adjacent the respective diodes and will operate to transmit heat through the housing to elevate the skin temperature of a subject during the treatment process. It is contemplated that the augmentation of the thermal treatment effect of the diodes provided by the resistance elements will only be utilized when switch 16 of device 10 is in a high setting. Thus when switch 16 is in a low setting, there will be no current flow through resistors 27, 29, 31, 33, 35 and 37 and both photo and thermal treatment effects will be provided by the diodes alone.

As previously noted, diodes 26, 28 and 30 are substantially equally spaced along the longitudinal midline of housing 12. Preferably diodes 26, 28 and 30 are positioned so as to place the longitudinal axis thereof substantially perpendicular to the tangent of the radius of curvature with a spacing specifically designed to accommodate the average human anatomy. In a preferred embodiment, the actual longitudinal spacing between diodes 26, 28 and 30 is about one inch which corresponds to the average distance between the knuckles of an adult human.

A single diode 32 is also provided at the extreme end of housing 12 and is positioned with its axis forming an acute included angle of preferably about 45° with the tangent to the radius of curvature although angulations in the range of from about 30° to about 60° may also be utilized. The primary purpose in the positioning and angulation of diode 32 is to provide for localized point treatment of areas of the anatomy which may not be easily accessible to the multiple diode array provided by the main treatment portion such as for example superficial body orifices (nares, eyelids, lips and part of the auricle (ear)—posterior, concha, helix, tragus, auricular insertion line on the face, lobule, superior hemi-concha, and internal face), point treatment of the fingers and toes, and the many concave body areas that lie between tendon, cartilage, and bones, i.e. the area between the distal tip of the fibula and the Achilles tendon, the area between the distal tip of the tibia and Achilles tendon, the nose, the inner and outer area of the olecranon process of the elbow, the tempera mandibular joint (TMJ) among others.

Additionally, diode 32 may be utilized in a "point finder" mode in order to assist in ascertaining specific treatment points. Use of diode 32 in a "point finder" mode results in a characteristic change in the arterial pulse known as Vascular Autonomic Signal.

Preferably light emitting diodes 26, 28, 30 and 32 will operate in the infrared frequency range and in a preferred embodiment will emit light frequency in the range of about 0.6 to 1.5 micrometers. The use of such infrared light emitting diodes and the current flow through the resistors will enable the device to apply therapeutic thermal treatment as well as photo treatment by facilitating a localized increase in skin temperature. In order to control this localized skin temperature increase, the device of the present invention is provided with a switch assembly 56 which enables selection of either a low or high heat range. In a preferred embodiment, it is anticipated that the low setting will operate the diodes only to provide skin temperature elevation in a range from about 32.6° C. to 42.5° C. whereas in a high setting, thermal treatment from the diodes will be augmented by heat from the resistors. This added resistance heating will result in skin temperature elevation in the range of about 32.6° C. to about 48° C. The actual skin temperature increases in either setting will be dependent upon the duration of treatment, however, it is anticipated that both settings will result in the maximum temperature rise being achieved with a treatment duration of about 15 minutes under normal ambient conditions.

As a result of the wave length of the light, and the frequency of pulsation, and the energy delivery from the diodes (joules of energy from the milliwattage of the diode) there results in the body a large number of physiologic responses. These physiological responses include for example acceleration of the production of procollagen resulting in enhanced collagen synthesis through selective action on collagen gene expression at the transcriptional level. This is a likely sequel to elevations of procollagen mRNA levels resulting in alterations in the chromatin structure. As a result of the increased collagen content and fibroblast cell population, photo-thermal treatment of device 10 produces a more rapid development of increased wound tensile strength—almost 100% by the fourth post-traumatic day thereby decreasing the likelihood of wound dehiscence.

There is increased cross-linking of existing collagen molecules and improved organization of functional collagen fibers. Also, photo-thermal treatment device 10 stimulates macrophages (a type of white blood cell) to release factors that stimulate fibroblast replication and proliferation (e.g. monokines). Cellular effects which occur include mitochondrial hyperplasia, the appearance of cytoplasmic microfilament bundles, and the deposition of an abundant fibrillar matrix in pericellular regions. A cellular phenotype of the fibroblast, the myofibroblast, is generated. This cell is found in granulation tissue; and its primary role occurs in the remodeling phase of wound healing, including contractile activity in addition to the synthesis of collagen. The photo-thermal treatment device 10 thereby accelerates the formation of a functional scar.

Energy delivered by photo-thermal treatment device 10 is absorbed at the mitochondrial level and is available for photochemical reactions which leads to an increase in oxidative enzyme activities. Photon absorption by cytochromes, which are present in large numbers in mitochondrial crests, result in an enhancement of protein synthesis producing increased substance for wound repair.

Use of photo-thermal treatment device 10 also accelerates epithelization across open wounds, which not only speeds the healing of the wound; but, also reduces the risk of secondary infection which would delay healing time and increase morbidity. Relief of the edema (swelling) allows approximation of the epithelial edges of the wound and further promotes wound healing.

Including and in addition to the above there are multiple biologic targets of photothermal treatment device 10 among which are: stimulation of ionic movements between intracellular and extracellular compartments, action on mitochondria via cytochrome oxidases, photoelectric action on cell membrane repolarization by a respiratory chain intermediary of the cytochrome, a photochemical effect on protein synthesis, an increase in RNA synthesis, and an action by resonance on DNA.

Application of photothermal treatment device 10 to the surface of painful soft tissue areas and open and closed wounds results in an increase in serotonin production and other neurotransmitter substances. Serotonin is a chemical precursor to endorphins, enkephlines, and dinorphines and subsequently increased levels of these naturally occurring "morphine like" products circulate in the body resulting in a reduction in pain.

Application of photo-thermal treatment device 10 also produces a relaxation of painful reflex muscle spasm by restoring normal muscle tissue properties on a cellular level through adenosine triphosphate (ATP) formation and enzyme activity. Relaxation of spastic muscles relieves the painful stimulation and irritation of A and C nerve fibers.

Additionally, application of photo-thermal treatment device 10 decreases sensory nerve conduction velocity which also contributes to pain reduction. Use of photo-thermal treatment device 10 appears to raise the perception threshold of sensory nerves which promotes a reduction in pain.

Further application of photo-thermal treatment device 10 to painful, swollen, stiff, non-septic joints reduces the pain, swelling, and erythema, and improves joint mobility and strength. These favorable effects result from the multiple mechanisms described above including the release of neurotransmitters, alternations in blood flow, cellular changes, alterations in neuronal transmittal and sensitivity, alterations in enzymatic activity.

It should also be noted that adaptation of the body to the photo-stimulation treatment results in degradation of the effectiveness thereof over even relatively brief periods of time. In order to reduce or minimize the ability of the body to adapt to such treatment and hence to maximize the effectiveness thereof, the present invention incorporates circuitry to sequentially pulse the light emitting diodes 26, 28, 30 and 32. While pulsing the diodes on and off at a set frequency lessens the rate at which the body is able to adapt to and hence reduce the effectiveness of the treatment, even greater resistance to body adaptation may be achieved by varying the frequency at which each diode is pulsed. In a preferred embodiment, it is anticipated that pairs of diodes will be pulsed sequentially with the frequency of pulses being in the range of about 277 to 307 cycles per second. More specifically, in the currently preferred embodiment of the present invention, diodes 28 and 32 will be energized simultaneously followed by the simultaneous energizing of diodes 26 and 30 as diodes 28 and 32 are deenergized. This sequential firing or energization of pairs of diodes greatly reduces the body's adaptation to the treatment which, as noted above, decreases the effectiveness of same without the need for more complicated and costly electronic circuitry.

It should be noted, however, that if desired more complex circuitry could be provided to cyclically fire or energize and deenergize each diode in a particular sequence rather than as pairs or even in a random sequencing of the firing order. Further, if desired, the duty cycle or on time versus off time could also be varied either by specific control or in a random manner.

As noted above, the lower portion of housing 12 is of a somewhat thicker dimension so as to accommodate switch assembly 56 and a power on/off switch assembly 58 which is preferably of the push on, push off type whereas switch 56 will preferably be a double pole type with push button switching between each of the poles. Actuator buttons 14 and 16 protrude through openings 52 and 50 provided in housing 12 and are biased outwardly by the respective switches. Preferably, both switches 56 and 58 will be mounted on a single circuit board 60 so as to facilitate assembly of the device which circuit board will also contain the necessary circuitry to accomplish the sequential firing of the respective diodes as well as to control the on/off and high/low switching of the apparatus.

Similarly, each of the diodes 26, 28, and 30 are also mounted to a separate circuit boards 62, 64, and 66 with circuit board 66 also containing a pair of low power indicator lights 68, 70 with light 68 indicating if the device is operating in the high or low temperature range and indicator light 70 indicating if the device is switched on. Diode 32 is also mounted on circuit board 66 and each of the circuit boards 62, 64, and 66 have pairs of resistors 27, 29; 31, 33; and 35, 37 mounted thereon as well as appropriate circuitry for selectively supplying power thereto as well as to the respective diodes. Lens 18 provided in housing 12 is positioned to overlie the indicator lights 68 and 70 so as to allow easy, convenient viewing of same from the back side of the device 10.

In order to securely mount circuit board 60 in housing 12, a pair of spaced substantially parallel raised flanges 72 and 74 are integrally formed in portion 38 in the thicker portion of housing 12. Each of these flanges included a generally flat support edge 76 extending longitudinally of the housing upon which circuit board 60 is designed to be seated as well as a pair of raised tab portions 78 and 80 at opposite the respective flanges. Circuit board 60 includes cut out corner portions 82 at each of the four corners thereof which are adapted to receive respective tab portions 78 and 80 so as to inhibit relative lateral and longitudinal movement between circuit board 60 and housing portion 38. In like manner, housing portion 38 also includes three additional pairs of integrally formed upstanding longitudinally extending laterally spaced flange portions 84, 86, 88, 90, 92 and 94 each of which includes a longitudinally extending supporting surface 96 upon which respective circuit boards 62, 64 and 66 are adapted to be supported and a pair of upstanding tab portions 98, 100 at opposite ends thereof. As with circuit board 60, each of circuit boards 62, 64 and 66 include cut out portions 101 at each of the four corners thereof which cut out portions are designed to receive respective tab portions 98 and 100 and to cooperate therewith to resist relative lateral and longitudinal movement between the circuit boards and housing portion 38.

In order to retain circuit boards 60, 62, 64 and 66 seat on respective flange portions 72, 74, 84, 86, 88, 90, 92 and 94 when housing portions 38 and 40 are secured together, housing portion 40 has integrally formed therewith suitably positioned raised flange portions 102, 104, 106 and 108 which are adapted to engage the surface of respective circuit boards 60, 62, 64 and 66 so as to retain them in assembled relationship with the respective flanges and tabs. It should be noted that diodes 26, 28 and 30 will preferably be positioned so as to protrude slightly outwardly from the housing so as to enable direct contact with the body surface being treated.

As mentioned above, the photo-thermal treatment device is designed to be used with a suitable external remote power supply such as for example a model CV-6500-2 manufactured by Chi Stock which utilizes a 120 volt 60 hz input and provides an output of 5.5 volts DC at 500 ma. Of course, any other suitable power supply may be used in place thereof. The circuitry required for sequentially energizing each of the pairs of diodes will preferably be incorporated into the switch carrying circuit board, it being understood that the specific circuitry is well known in the art and hence not described in detail herein.

Referring once again to FIGS. 1 and 2, it is noted that the photo-thermal treatment device of the present invention is specifically ergonomically shaped to promote ease of use as well as to adapt it for use in treating a wide variety of body surface portions. To this end, the upper treatment portion is not only accurately shaped as noted above but also tapers to the upper end thereof further enhancing the ability of the point diode 32 to be used in treatment of difficult to reach localized areas. The enlarged lower portion of the housing facilitates hand grasping and holding of the device during treatment.

While it will be apparent that the preferred embodiment of the invention disclosed is well calculated to provide the advantages and features above stated, it will be appreciated that the invention is susceptible to modification, variation and change without departing from the proper scope or fair meaning of the subjoined claims.

We claim:

1. A photo-thermal treatment device for applying light and heat stimulation to a surface of a human body comprising:
   a substantially rigid non-flexible housing having a generally arcuate concave surface and a generally convex surface;
   a plurality of light emitting diodes projecting outwardly from said concave surface, said diodes being positioned in spaced relationship;
   a circuit in said housing operative to selectively energize said light emitting diodes, whereby only selective diodes are energized at any given time, said sequential energizing of said light emitting diodes being operative to inhibit body adaptation to said stimulation and thereby enhance the effectiveness of said stimulation.

2. A photo-thermal treatment device as set forth in claim 1 wherein said convex surface has a radius of curvature selected to generally conform to various surfaces of a human body.

3. A photo-thermal treatment device as set forth in claim 2 wherein said light emitting diodes emit light in the infrared spectrum.

4. A photo-thermal treatment device as set forth in claim 1 wherein said light emitting diodes include first and second pairs of light emitting diodes, said first and second pairs of diodes being energized in alternating sequence.

5. A photo-thermal treatment device as set forth in claim 1 further comprising heating elements selectively operable to augment the thermal treatment provided by said diodes.

6. A photo-thermal treatment device as set forth in claim 5 wherein said heating elements comprise resistive elements positioned in close proximity to at least certain ones of said plurality of diodes.

7. A photo-thermal treatment device as set forth in claim 5 wherein said housing includes a switch operable to select between a first lower power level and second higher power level, said heating elements being energized when said higher power level is selected.

8. A photo-thermal treatment device as set forth in claim 7 wherein said housing includes an indicator operative to provide an indication of the selection between said first and second power levels.

9. A photo-thermal treatment device as set forth in claim 1 wherein said light emitting diodes each have a longitudinal axis, said longitudinal axis extending substantially perpendicular to a line tangent to said radius of curvature at respective of said diodes.

10. A photo-thermal treatment device as set forth in claim 8 wherein said housing includes an additional diode positioned in spaced relationship to said plurality of diodes, said additional diode having a longitudinal axis extending at an actual angle relative to a line tangent to said radius of curvature at said additional diode.

11. A photo-thermal treatment device as set forth in claim 9 wherein said additional diode is positioned adjacent one end of said housing and is adapted to provide localized point photo-thermal stimulation.

12. A photo-thermal treatment device as set forth in claim 1 wherein said concave surface has a radius of curvature equal to approximately 4.5 inches.

13. A photo-thermal treatment device as set forth in claim 1 wherein said plurality of light emitting diodes are substantially equally spaced.

14. A photo-thermal treatment device as set forth in claim 13 wherein the spacing between said diodes is between about 0.9 to 1.1 inches.

15. A photo-thermal treatment device as set forth in claim 1 wherein each of said plurality of light emitting diodes are supported on a circuit board and said housing includes mounting portions operative to fixedly support said circuit boards thereon.

16. A photo-thermal treatment device as set forth in claim 15 wherein said mounting portions are integrally formed in said housing.

17. A photo-thermal treatment device for use in applying light and thermal stimulation to the surface of a body, said device comprising:

an elongated arcuate shaped housing having a concave surface and a convex surface, the concave surface having a radius of curvature within the range of approximately 4 to 5 inches;

a plurality of substantially equally spaced light emitting diodes projecting outwardly from said concave surface, said light emitting diodes being positioned generally along a line extending substantially parallel to the longitudinal axis of said housing;

circuitry within said housing for sequentially energizing said light emitting diodes in a random varying frequency such that only selected ones of said light emitting diodes are energized at a given time whereby the frequency of energization of each diode will be continuously varied to thereby inhibit body adaptation to said stimulation; and a power supply for supplying power to said circuitry.

18. A photo-thermal treatment device as set forth in claim 17 further comprising heating elements selectively operable to augment the thermal treatment provided by said plurality of diodes, said device including switch means operable to energize said heating elements when in a first position and to deenergize said heating elements when in a second position.

19. A photo-thermal treatment device as set forth in claim 18 wherein said heating elements comprise resistive elements, said resistive elements being positioned in pairs adjacent opposite sides of certain ones of said light emitting diodes.

* * * * *

UNITED STATES PATENT AND TRADEMARK OFFICE
CERTIFICATE OF CORRECTION

PATENT NO.     : 6,187,029 B1
DATED          : February 13, 2001
INVENTOR(S)    : Ronald S. Shapiro et al.

It is certified that error appears in the above-identified patent and that said Letters Patent is hereby corrected as shown below:

Column 7, claim 10,
Line 38, "8" should be -- 9 --.

Column 7, claim 11,
Line 44, "9" should be -- 10 --.

Signed and Sealed this

Thirteenth Day of November, 2001

*Attest:*

NICHOLAS P. GODICI
*Attesting Officer*   *Acting Director of the United States Patent and Trademark Office*